(12) United States Patent
Sanchez

(10) Patent No.: US 11,571,184 B2
(45) Date of Patent: Feb. 7, 2023

(54) ULTRASOUND DEVICE WITH ELEVATIONAL BEAMFORMING

(71) Applicant: BFLY OPERATIONS, INC., Burlington, MA (US)

(72) Inventor: Nevada J. Sanchez, Guilford, CT (US)

(73) Assignee: BFLY OPERATIONS, INC., Burlington, MA (US)

(*) Notice: Subject to any disclaimer, the term of this patent is extended or adjusted under 35 U.S.C. 154(b) by 0 days.

(21) Appl. No.: 16/837,945

(22) Filed: Apr. 1, 2020

(65) Prior Publication Data

US 2020/0315586 A1 Oct. 8, 2020

Related U.S. Application Data

(60) Provisional application No. 62/828,603, filed on Apr. 3, 2019.

(51) Int. Cl.
*A61B 8/08* (2006.01)
*A61B 8/00* (2006.01)

(52) U.S. Cl.
CPC ............. *A61B 8/5207* (2013.01); *A61B 8/42* (2013.01); *A61B 8/4494* (2013.01); *A61B 8/54* (2013.01)

(58) Field of Classification Search
CPC ........... A61B 8/54; A61B 8/4494; A61B 8/42; A61B 8/5207; G01S 7/52026; G01S 7/5208; G01S 15/8925; G10K 11/346

See application file for complete search history.

(56) References Cited

U.S. PATENT DOCUMENTS

| 4,983,970 A | * | 1/1991 | O'Donnell | G10K 11/346 |
| | | | | 341/122 |
| 5,544,128 A | * | 8/1996 | Kim | G01S 7/52095 |
| | | | | 367/103 |

(Continued)

FOREIGN PATENT DOCUMENTS

| GB | 2352346 A | * | 1/2001 | ........... G06F 1/0328 |
| KR | 20160070603 A | * | 6/2016 | |
| WO | WO 2017/222964 A1 | | 12/2017 | |

OTHER PUBLICATIONS

KR-20160070603-A (Year: 2016).*

(Continued)

*Primary Examiner* — Joel Lamprecht
*Assistant Examiner* — Nyrobi Celestine
(74) *Attorney, Agent, or Firm* — Carter, DeLuca & Farrell LLP

(57) ABSTRACT

Aspects of the technology described herein relate to apparatuses and methods for performing elevational beamforming of ultrasound data. Elevational beamforming may be implemented by different types of control circuitry. Certain control circuitry may be configured to control memory such that ultrasound data from different elevational channels is summed with stored ultrasound data in the memory that was collected at different times. Certain control circuitry may be configured to control a decimator to decimate ultrasound data from different elevational channels with different phases. Certain control circuitry may be configured to control direct digital synthesis circuitry to add a different phase offset to complex signals generated by the DDS circuitry for multiplying with ultrasound data from different elevational channels.

19 Claims, 13 Drawing Sheets

(56) References Cited

U.S. PATENT DOCUMENTS

| | | | |
|---|---|---|---|
| 5,600,675 A * | 2/1997 | Engeler | G01S 7/527 367/7 |
| 5,790,072 A * | 8/1998 | Gerveshi | H04N 21/242 341/141 |
| 6,544,175 B1 | 4/2003 | Newman | |
| 7,658,713 B2 | 2/2010 | Barnes et al. | |
| 7,927,300 B2 | 4/2011 | Tanaka | |
| 8,248,885 B2 | 8/2012 | Ma et al. | |
| 9,088,404 B2 | 7/2015 | Glende, Jr. | |
| 9,100,044 B2 * | 8/2015 | Mazumdar | H03M 9/00 |
| 9,229,097 B2 | 1/2016 | Rothberg et al. | |
| 9,327,142 B2 | 5/2016 | Rothberg et al. | |
| 9,521,991 B2 | 12/2016 | Rothberg et al. | |
| 9,592,030 B2 | 3/2017 | Rothberg et al. | |
| 9,608,598 B1 | 3/2017 | Melanson | |
| 9,736,579 B2 * | 8/2017 | Tattler | H03K 7/08 |
| 10,695,034 B2 | 6/2020 | Ralston et al. | |
| 2004/0236206 A1 | 11/2004 | Sakas et al. | |
| 2007/0067123 A1 | 3/2007 | Jungerman | |
| 2010/0097057 A1 | 4/2010 | Karpen | |
| 2011/0055447 A1 | 3/2011 | Costa | |
| 2011/0116654 A1 * | 5/2011 | Chan | G10K 11/17854 381/94.8 |
| 2014/0347201 A1 | 11/2014 | Barrenscheen | |
| 2015/0280841 A1 * | 10/2015 | Gudovskiy | H04L 27/0014 375/226 |
| 2016/0157827 A1 * | 6/2016 | Kristoffersen | A61B 8/5207 600/443 |
| 2016/0228092 A1 * | 8/2016 | Kim | G01S 7/52084 |
| 2017/0184716 A1 * | 6/2017 | Bini | G01S 7/52047 |
| 2017/0360399 A1 | 12/2017 | Rothberg et al. | |
| 2018/0070917 A1 | 3/2018 | Rothberg et al. | |
| 2019/0247019 A1 * | 8/2019 | Savord | G01S 7/5208 |
| 2019/0343485 A1 * | 11/2019 | Shepard | A61B 8/4488 |

OTHER PUBLICATIONS

International Search Report and Written Opinion dated Jun. 23, 2020 in connection with International Application No. PCT/US2020/026138.

* cited by examiner

ULTRASOUND DEVICE WITH ELEVATIONAL BEAMFORMING

CROSS-REFERENCE TO RELATED APPLICATIONS

The present application claims the benefit under 35 U.S.C. § 119(e) of U.S. Patent Application Ser. No. 62/828,603, filed Apr. 3, 2019, and entitled "METHODS AND APPARATUSES FOR ELEVATIONAL BEAMFORMING OF ULTRASOUND DATA," which is hereby incorporated herein by reference in its entirety.

FIELD

Generally, the aspects of the technology described herein relate to collection of ultrasound data. Some aspects relate to methods and apparatuses for elevational beamforming of ultrasound data.

BACKGROUND

Ultrasound probes may be used to perform diagnostic imaging and/or treatment, using sound waves with frequencies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image. Many different types of images can be formed using ultrasound devices. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to one aspect, an ultrasound device is provided, comprising: processing circuitry; and control circuitry configured to control the processing circuitry to perform elevational beamforming, wherein the control circuitry and the processing circuitry are disposed on an ultrasound-on-a-chip in the ultrasound device.

According to one aspect, an ultrasound device is provided, comprising: processing circuitry that comprises: a memory; a decimator; direct digital synthesis (DDS) circuitry; and control circuitry. The control circuitry comprises at least two of: first control circuitry configured to control the memory such that first ultrasound data from a first elevational channel that was collected at a first time is summed with stored ultrasound data in the memory that was collected at a second time, and second ultrasound data from a second elevational channel that was collected at the first time is summed with stored ultrasound data in the memory that was collected at a third time; second control circuitry configured to control the decimator to decimate the first ultrasound data from the first elevational channel with a first phase and to decimate the second ultrasound data from the second elevational channel with a second phase; and third control circuitry configured to control the DDS circuitry to add a first phase offset to a complex signal generated by the DDS circuitry for multiplying with first ultrasound data from the first elevational channel and to add a second phase offset to the complex signal generated by the DDS circuitry for multiplying with second ultrasound data from the second elevational channel. At least two of the first control circuitry, the second control circuitry, and the third control circuitry are each configured to control the processing circuitry to implement a portion of a delay of ultrasound data from one of the first and second elevational channels.

According to one aspect, an apparatus for performing elevational beamforming of ultrasound data comprises a memory and control circuitry configured to control the memory such that first ultrasound data from a first elevational channel that was collected at a first time is summed with stored ultrasound data in the memory that was collected at a second time, and second ultrasound data from a second elevational channel that was collected at the first time is summed with stored ultrasound data in the memory that was collected at a third time.

In some embodiments, the control circuitry is configured to control an address for reading the stored ultrasound data from the memory and for writing the summed ultrasound data to the memory. In some embodiments, the memory further comprises an address counter, the control circuitry is configured to provide a value to the memory, and the address for reading the stored ultrasound data from the memory and for writing the summed ultrasound data to the memory is a sum of a current value of the address counter and the value provided by the control circuitry. In some embodiments, the apparatus further comprises a register storing a plurality of values each corresponding to one of the first and second elevational channels, and the control circuitry is configured to retrieve the value from amongst the plurality of values. In some embodiments, the value comprises a fixed value that does not change during acquisition of the ultrasound data from the first and second elevational channels. In some embodiments, the value comprises a dynamic value that changes during acquisition of the ultrasound data from the first and second elevational channels. In some embodiments, the apparatus further comprises dynamic delay generation circuitry configured to calculate the dynamic value in real-time. In some embodiments, the apparatus further comprises dynamic delay generation circuitry configured to calculate the dynamic value using a CORDIC algorithm. In some embodiments, the apparatus further comprises dynamic delay generation circuitry configured to calculate the dynamic value using piecewise approximation. In some embodiments, the apparatus further comprises storage for storing the dynamic value before the acquisition of the ultrasound data.

According to another aspect, an apparatus for performing elevational beamforming of ultrasound data comprises a decimator and control circuitry configured to control the decimator to decimate first ultrasound data from a first elevational channel with a first phase and to decimate second ultrasound data from a second elevational channel with a second phase.

In some embodiments, the decimator includes a counter for determining when the decimator outputs samples and the control circuitry is configured to provide a value to the counter. In some embodiments, the decimator includes one counter per elevational channel. In some embodiments, the apparatus further comprises a register storing a plurality of values each corresponding to one of the first and second elevational channels, and the control circuitry is configured to retrieve the value from amongst the plurality of values. In some embodiments, the value comprises a fixed value that does not change during acquisition of the ultrasound data from the first and second elevational channels. In some embodiments, the control circuitry is further configured to provide a dynamic value to the counter for adding or subtracting from the counter, wherein the dynamic value changes during acquisition of the ultrasound data from the first and second elevational channels. In some embodiments, the apparatus further comprises dynamic delay generation circuitry configured to calculate the dynamic value in real-time. In some embodiments, the apparatus further comprises dynamic delay generation circuitry configured to calculate the dynamic value using a CORDIC algorithm. In some embodiments, the apparatus further comprises dynamic delay generation circuitry configured to calculate the dynamic value using piecewise approximation. In some embodiments, the apparatus further comprises storage for storing the dynamic value before the acquisition of the ultrasound data. In some embodiments, the apparatus further comprises a cascaded integrator-comb (CIC) filter that includes the decimator. In some embodiments, the CIC filter includes a subtractor and a delay stage in a feedforward configuration following the decimator. In some embodiments, the control circuitry is further configured to control the decimator to clock samples into the subtractor and the delay register at different clock cycles. In some embodiments, the apparatus further comprises a cascaded integrator-comb (CIC) filter that includes the decimator, the CIC filter includes a subtractor and a delay stage in a feedforward configuration following the decimator, and the control circuitry is further configured to control the decimator to clock samples into the subtractor and the delay register at different clock cycles based on the dynamic value.

According to another aspect, an apparatus for performing elevational beamforming of ultrasound data comprises direct digital synthesis (DDS) circuitry and control circuitry configured to control the DDS circuitry to add a first phase offset to a complex signal generated by the DDS circuitry for multiplying with first ultrasound data from a first elevational channel and to add a second phase offset to the complex signal generated by the DDS circuitry for multiplying with second ultrasound data from a second elevational channel.

In some embodiments, the DDS circuitry includes a DDS phase counter and the control circuitry is configured to provide a value to the DDS phase counter. In some embodiments, the DDS circuitry includes one DDS phase counter per elevational channel. In some embodiments, the apparatus further comprises a register storing a plurality of values each corresponding to one of the first and second elevational channels and the control circuitry is configured to retrieve the value from amongst the plurality of values. In some embodiments, the value comprises a fixed value that does not change during acquisition of the ultrasound data from the first and second elevational channels. In some embodiments, the control circuitry is further configured to provide a dynamic value to the DDS phase counter for adding or subtracting from the DDS phase counter, wherein the dynamic value changes during acquisition of the ultrasound data from the first and second elevational channels. In some embodiments, the apparatus further comprises dynamic delay generation circuitry configured to calculate the dynamic value in real-time. In some embodiments, the apparatus further comprises dynamic delay generation circuitry configured to calculate the dynamic value using a CORDIC algorithm. In some embodiments, the apparatus further comprises dynamic delay generation circuitry configured to calculate the dynamic value using piecewise approximation. In some embodiments, the apparatus further comprises storage for storing the dynamic values before the acquisition of the ultrasound data.

According to another aspect, an apparatus for performing elevational beamforming of ultrasound data comprises a memory, a decimator, direct digital synthesis (DDS) circuitry, and control circuitry comprising at least two of first control circuitry configured to control the memory such that first ultrasound data from a first elevational channel that was collected at a first time is summed with stored ultrasound data in the memory that was collected at a second time, and second ultrasound data from a second elevational channel that was collected at the first time is summed with stored ultrasound data in the memory that was collected at a third time; second control circuitry configured to control the decimator to decimate the first ultrasound data from the first elevational channel with a first phase and to decimate the second ultrasound data from the second elevational channel with a second phase; and third control circuitry configured to control the DDS circuitry to add a first phase offset to a complex signal generated by the DDS circuitry for multiplying with first ultrasound data from a first elevational channels and to add a second phase offset to the complex signal generated by the DDS circuitry for multiplying with second ultrasound data from a second elevational channel. At least two of the first control circuitry, the second control circuitry, and the third control circuitry are each configured to implement a portion of a delay of ultrasound data from one of the first and second elevational channels.

In some embodiments, a first resolution of delays implemented by the first control circuitry is less than a second resolution of delays implemented by the second control circuitry. In some embodiments, a first resolution of delays implemented by the first control circuitry is less than a third resolution of delays implemented by the third control circuitry. In some embodiments, a second resolution of delays implemented by the second control circuitry is less than a third resolution of delays implemented by the third control circuitry. In some embodiments, the apparatus further comprises at least one analog-to-digital converter (ADC) configured to digitally convert the ultrasound data from the first and second elevational channels at a rate of $f_{ADC}$, a decimation rate of the decimator is D, and a first resolution of delays implemented by the first control circuitry is $D/f_{ADC}$. In some embodiments, the apparatus further comprises at least one analog-to-digital converter (ADC) configured to digitally convert the ultrasound data from the first and second elevational channels at a rate of $f_{ADC}$, and a second resolution of delays implemented by the second control circuitry is $1/f_{ADC}$. In some embodiments, the DDS circuitry is configured to generate a sinusoidal waveform having a frequency $f_{DDS}$, the DDS circuitry includes a DDS phase counter having a resolution of $B_{DDS}$, and a third resolution of delays implemented by the third control circuitry is $1/(f_{DDS}B_{DDS})$.

In some embodiments, the delay includes a first delay portion comprising the delay truncated to a nearest multiple of a first resolution of the first control circuitry, leaving a first remainder, wherein the first delay portion is implemented by the first control circuitry; a second delay portion comprising the first remainder truncated to a nearest multiple of a second resolution of the second control circuitry, leaving a second remainder, wherein the second delay portion is implemented by the second control circuitry; and a third delay portion comprising the second remainder truncated to a nearest multiple of a third resolution of the third control circuitry, wherein the third delay portion is implemented by the third control circuitry. In some embodiments, the delay includes:

a first delay portion comprising the delay truncated to a nearest multiple of a first resolution of the first control circuitry, leaving a first remainder, wherein the first delay portion is implemented by the first control circuitry; and a second delay portion comprising the first remainder truncated to a nearest multiple of a second resolution of the second control circuitry, leaving a second remainder, wherein the second delay portion is implemented by the second control circuitry. In some embodiments, the delay includes a first delay portion comprising the delay portion truncated to a nearest multiple of a first resolution of the first control circuitry, leaving a first remainder, wherein the first delay portion is implemented by the first control circuitry; and a third delay portion comprising the first remainder truncated to a nearest multiple of a third resolution of the third control circuitry, wherein the third delay portion is implemented by the third control circuitry. In some embodiments, the delay includes a second delay portion comprising the delay truncated to a nearest multiple of a second resolution of the second control circuitry, leaving a second remainder, wherein the second delay portion is implemented by the second control circuitry; and a third delay portion comprising the second remainder truncated to a nearest multiple of a third resolution of the third control circuitry, wherein the third delay portion is implemented by the third control circuitry.

According to another aspect, an apparatus for performing elevational beamforming of ultrasound data comprises a memory, direct digital synthesis (DDS) circuitry, and control circuitry comprising first control circuitry configured to control the memory such that first ultrasound data from a first elevational channel that was collected at a first time is summed with stored ultrasound data in the memory that was collected at a second time, and second ultrasound data from a second elevational channel that was collected at the first time is summed with stored ultrasound data in the memory that was collected at a third time; and second control circuitry configured to control the DDS circuitry to add a first phase offset to a complex signal generated by the DDS circuitry for multiplying with the first ultrasound data from the first elevational channels and to add a second phase offset to the complex signal generated by the DDS circuitry for multiplying with the second ultrasound data from the second elevational channel, wherein the first control circuitry and the second control circuitry are each configured to implement a portion of a delay of ultrasound data from one of the first and second elevational channels.

In some embodiments, a first resolution of delays implemented by the first control circuitry is less than a second resolution of delays implemented by the second control circuitry. In some embodiments, the apparatus further comprises at least one analog-to-digital converter (ADC) configured to digitally convert the ultrasound data from the first and second elevational channels at a rate of $f_{ADC}$, a decimation rate of the decimator is D, and a first resolution of delays implemented by the first control circuitry is $D/f_{ADC}$.

In some embodiments, the DDS circuitry is configured to generate a sinusoidal waveform having a frequency $f_{DDS}$, the DDS circuitry includes a DDS phase counter having a resolution of $B_{DDS}$, and a second resolution of delays implemented by the second control circuitry is $1/(f_{DDS}B_{DDS})$. In some embodiments, the delay includes a first delay portion comprising the delay truncated to a nearest multiple of a first resolution of the first control circuitry, leaving a first remainder, wherein the first delay portion is implemented by the first control circuitry; and a second delay portion comprising the first remainder truncated to a nearest multiple of a second resolution of the second control circuitry, leaving a second remainder, wherein the second delay portion is implemented by the second control circuitry.

According to another aspect, an apparatus comprises control circuitry for controlling processing circuitry in a handheld ultrasound probe to perform elevational beamforming. In some embodiments, the control circuitry and the processing circuitry are disposed on an ultrasound-on-a-chip in the handheld ultrasound probe.

According to another aspect, an apparatus comprises control circuitry for controlling processing circuitry to perform elevational beamforming on ultrasound data, wherein the processing circuitry is in a portion of a datapath that is subsequent to conversion of the ultrasound data from analog to digital and prior to saving of the ultrasound data to memory.

Some aspects include a method to perform the actions that the apparatus is configured to perform.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

DETAILED DESCRIPTION

Recent advances in ultrasound technology have enabled large arrays of ultrasound transducers (with a large number of transducers along both the elevational and azimuthal dimensions) to be incorporated onto an integrated circuit to form an ultrasound-on-a-chip. Such an ultrasound-on-a-chip can form the core of a handheld ultrasound probe. The large ultrasound transducer array may allow such handheld ultrasound probes to have advanced functionality in terms of imaging techniques and clinical uses. For further description of an ultrasound-on-a-chip, see U.S. patent application Ser. No. 15/626,711 titled "UNIVERSAL ULTRASOUND IMAGING DEVICE AND RELATED APPARATUS AND METHODS," filed on Jun. 19, 2017 and published as U.S. Pat. App. Publication No. 2017-0360399 A1 (and assigned to the assignee of the instant application), which is incorporated by reference herein in its entirety.

Certain imaging techniques, such as three-dimensional ultrasound imaging, may require beamforming of ultrasound data along the elevational dimension of an ultrasound array. While conventional elevational beamforming may be performed on a host device to which an ultrasound probe is coupled, and may be performed in the analog domain or after saving of digital data to memory, this disclosure describes how processing circuitry that is already part of the datapath of an ultrasound-on-a-chip, and in particular a portion of the datapath subsequent to conversion of analog ultrasound data to digital but prior to saving of ultrasound data to memory, may be augmented with control circuitry configured to control the processing circuitry to implement elevational beamforming. For example, control circuitry may control memory, filters, and other signal processing circuitry to perform beamforming in addition to their standard operations. Thus, elevational beamforming may be performed on an ultrasound probe itself, and in particular on an ultrasound-on-a-chip, and the amount of extra circuitry needed to perform elevational beamforming may be reduced.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

Figure 1:
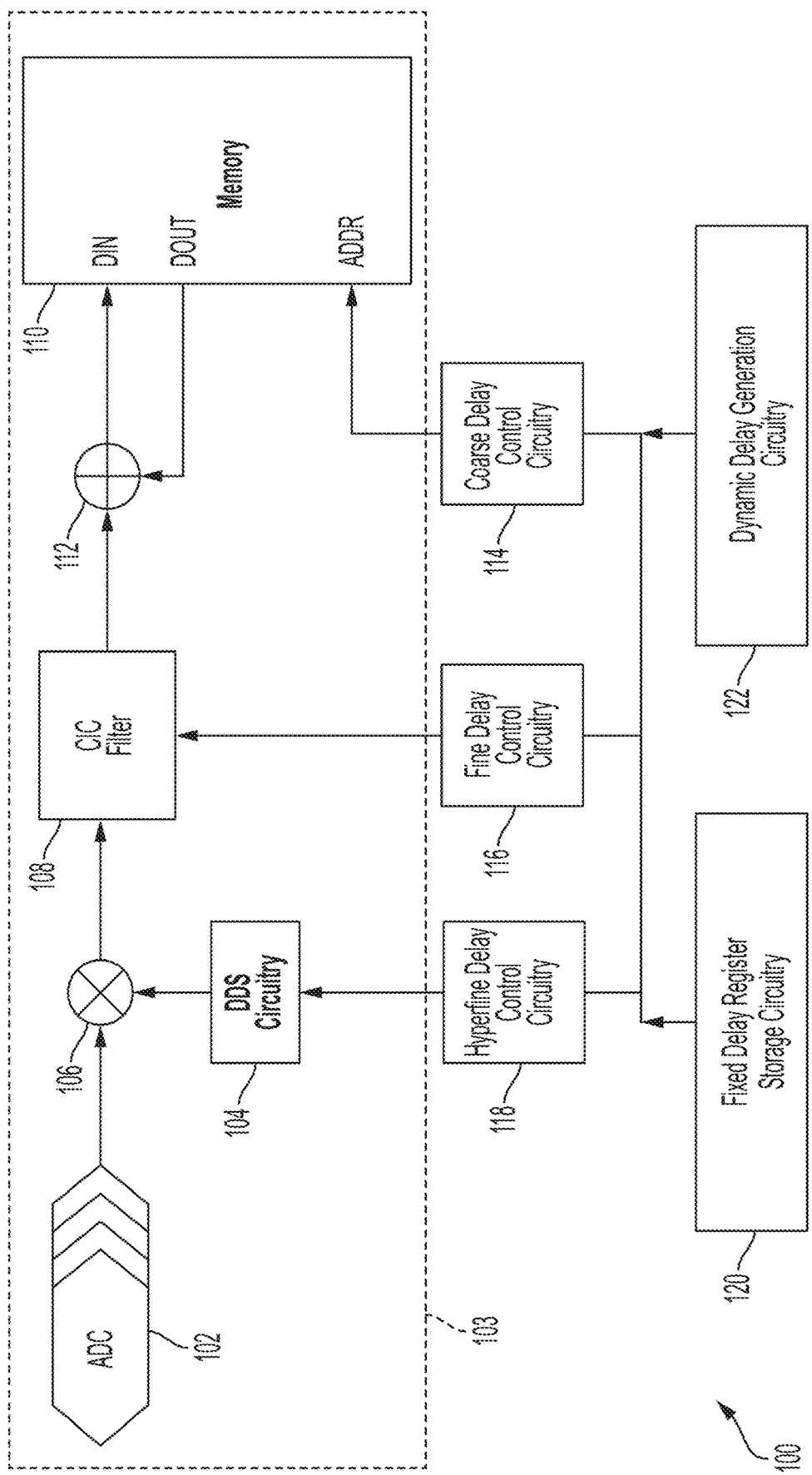
FIG. 1 illustrates an example datapath for ultrasound data received by an ultrasound device, in accordance with certain embodiments described herein.

FIG. 1 illustrates an example datapath 100 for ultrasound data received by an ultrasound device. The ultrasound device may include an array of ultrasound transducers having an azimuthal dimension and an elevational dimension. The azimuthal dimension may be the dimension of the transducer array that is parallel to the primary slice direction of ultrasound images formed by the ultrasound device. The elevational dimension may be the dimension of the transducer array that is orthogonal to the primary slice direction of ultrasound images formed by the ultrasound device. The datapath 100 includes processing circuitry 103, coarse delay control circuitry 114, fine delay control circuitry 116, hyperfine delay control circuitry 118, fixed delay register storage circuitry 120, and dynamic delay generation circuitry 122. The processing circuitry 103 comprises analog-to-digital converters (ADCs) 102, direct digital synthesis (DDS) circuitry 104, a multiplier 106, a cascaded integrator-comb (CIC) filter 108, memory 110, and an adder 112. All the circuitry of the datapath 100 may be in an ultrasound-on-a-chip device in a handheld ultrasound probe, or another type of ultrasound device such as a patch or pill.

It should be appreciated that in some embodiments, there may be some sharing of circuitry in the datapath 100, and/or there may be more instances of each component than shown in FIG. 1. For example, in some embodiments, there may be one multiplier 106 and one CIC filter 108 for every two ADCs 102.

The outputs of the ADCs 102 are coupled to one input of the multiplier 106. The output of the DDS circuitry 104 is coupled to a second input of the multiplier 106. The output of the multiplier 106 is coupled to the input of the CIC filter 108. The output of the CIC filter 108 is coupled to one input of the adder 112. The output of the adder 112 is coupled to a data-in (DIN) terminal of the memory 110. A data-out (DOUT) terminal of the memory 110 is coupled to a second input of the adder 112. The hyperfine delay control circuitry 118 is coupled to an input of the DDS circuitry 104. The fine delay control circuitry 116 is coupled to an input of the CIC filter 108. The coarse delay control circuitry 114 is coupled to an address (ADDR) input of the memory 110. The fixed delay register storage circuitry 120 is coupled to inputs of the hyperfine delay control circuitry 118, the fine delay control circuitry 116, and the coarse delay control circuitry 114. The dynamic delay generation circuitry 122 is coupled to inputs of the hyperfine delay control circuitry 118, the fine delay control circuitry 116, and the coarse delay control circuitry 114.

The ADCs 102 may be configured to convert analog ultrasound data to digital ultrasound data. Each of the ADCs 102 may be configured to convert analog ultrasound data received by a different elevational channel. For example, there may be multiple ultrasound transducers at different positions along the elevational dimension of an ultrasound transducer array, and each of the ADCs 102 may be configured to convert ultrasound data from one of the ultrasound transducers. As another example, there may be multiple groups of ultrasound transducers at different positions along the elevational dimension of an ultrasound transducer array, and each of the ADCs 102 may be configured to convert ultrasound data from one of the groups of ultrasound transducers. While FIG. 1 illustrates four ADCs 102 for four elevational channels, there may be more or fewer elevational channels and thus more or fewer ADCs 102.

The DDS circuitry 104 may be configured to translate the frequency of the ultrasound data from the ADCs 102 (after it has been digitized). For example, if the ultrasound data from the ADCs 102 occupies a certain band of frequencies, the DDS circuitry 104 may be configured to modulate the ultrasound data from the ADCs 102 such that it occupies a different band of frequencies, for example a band of frequencies with a lower center frequency. The DDS circuitry 104 may be configured to generate digital sinusoidal waveforms for forming a complex signal $e^{-i\omega_{DDS}t}$, where $\omega_{DDS}=2\pi f_{DDS}$ is the center frequency of interest. To generate these digital sinusoidal waveforms, the DDS circuitry 104 may include a DDS phase counter (or, as will be described below, more than one DDS phase counter). The value of the DDS phase counter may be used in sine and/or cosine lookup circuits to generate the sine and cosine portions of the complex signal $e^{-i\omega_{DDS}t}$. The increment value of the DDS phase counter may be proportional to $1/\omega_{DDS}$.

The multiplier 106 may be configured to multiply the ultrasound data from the ADCs 102 (after it has been digitized) with the complex signal $e^{-i\omega_{DDS}t}$ using the sinusoidal waveforms generated by the DDS circuitry. In particular, to realize this multiplication, the multiplier 106 may use quadrature modulation.

The CIC filter 108 may be configured to filter the ultrasound data (after it has been modulated). In some embodiments, the CIC filter 108 may be configured as a low-pass filter to remove high frequency images of the ultrasound data.

As described above, multiple ADCs 102 may share a single multiplier 106 and CIC filter 108. For example, there may be one multiplier 106 and one CIC filter 108 for every two ADCs 102. In this example, each multiplier 106 and CIC filter may be clocked at four times the ADC 102 conversion rate. This is because the multiplication step may be preceded by transformation of the real valued signal from an ADC 102 into "in phase" (real) and "out of phase" (complex) parts. Thus, the output of two ADCs 102 may result in two real and two imaginary signals, for a total of 4 signals that are processed at four times the ADC 102 conversion rate. Each of these signals may then pipeline into the multiplication stage of a single multiplier 106 and then into the CIC filter 108.

Figure 2:
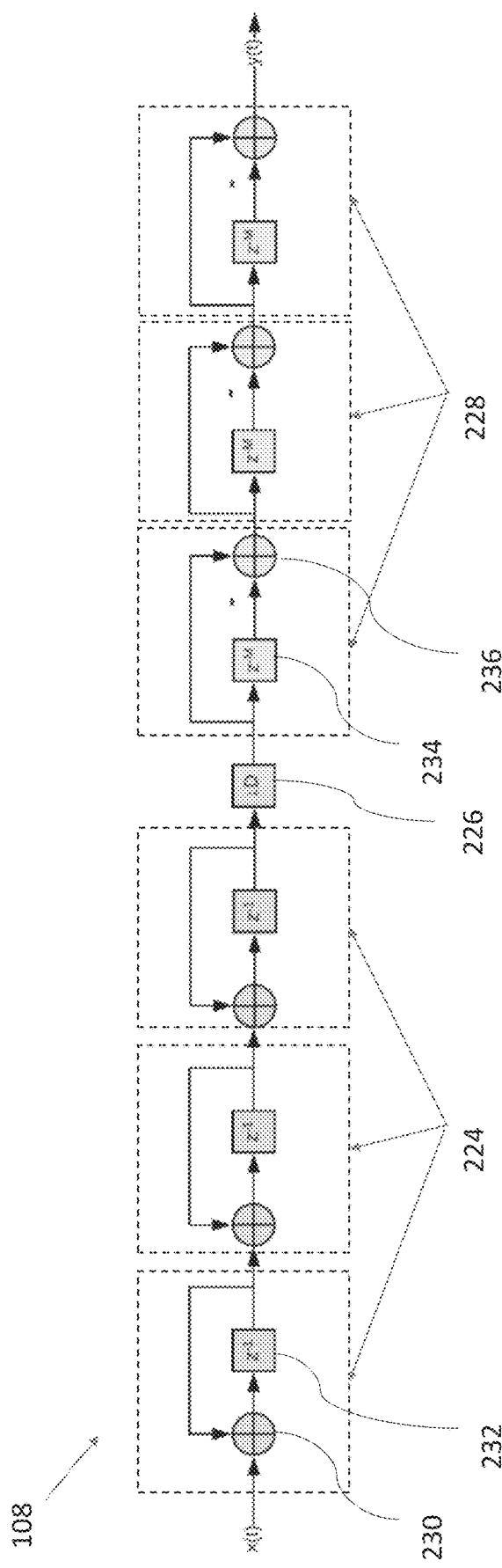
FIG. 2 illustrates a cascaded integrator-comb (CIC) filter in the datapath of FIG. 1 in more detail, in accordance with certain embodiments described herein.

FIG. 2 illustrates the CIC filter 108 in more detail, in accordance with certain embodiments described herein. The CIC filter 108 includes a series of integrator stages 224, followed by a decimator 226, followed by a series of comb stages 228. Each of the integrator stages 224 includes a delay stage 232 with delay 1 and an adder 230 in a feedback configuration. Each of the comb stages 224 includes a delay stage 234 with delay M and a subtractor 236 in a feedforward configuration. The CIC filter 108 is configured to filter a signal x(t) to produce a filtered signal y(t). The decimator 226 has a decimation rate of D. Thus, if the rate of the ultrasound data at the input of the CIC filter 108 is $f_{ADC}$ (i.e., the sampling rate of the ADCs 102), then the rate of the ultrasound data at the output of the CIC filter 108 (and thus at the input of the memory 110) may be $f_{ADC}/D$. The decimator 226 may include a counter (or, as will be described below, more than one counter) that counts from 0 to a threshold value at the rate of the ultrasound data entering the CIC filter 108, and when the counter reaches the threshold value, the decimator 226 may sample the ultrasound data from the last of the integrator stages 224, output that sample to the first of the comb stages 228, and reset the counter.

Returning to FIG. 1, the memory 110 may be configured to store the ultrasound data (after it has been filtered). In some embodiments, the memory 110 may be configured as a static random-access memory (SRAM), although other types of memory may be used. The memory 110 may include an address counter that increments based on a clock running at the rate of the ultrasound data being inputted to the memory 110 (in particular, $f_{ADC}/D$). The memory 110 may be configured to output, at the DOUT terminal, data stored in the memory 110 at an address that is the sum of the address counter and the data provided at the ADDR terminal. The memory 110 may be configured to write to the memory 110, at the address that is the sum of the address counter and the data provided at the ADDR terminal, the data inputted at the DIN terminal.

The adder 112 may be configured to add the ultrasound data (after it has been filtered) to data at the DOUT output of the memory 110 that has been retrieved from a particular address (based on the ADDR terminal) of the memory 110 and provide the sum at the DIN input of the memory 110 to be written to the same address of the memory 110. Thus, the adder 112 and memory 110 may be configured as accumulation circuitry. If the data provided at the ADDR terminal is 0, then the memory 110 may accumulate data the current address in the memory 110. If the data provided at the ADDR terminal is not zero, then the memory 110 may accumulate data an address that is before or after the current address in the memory 110.

The coarse delay control circuitry 114, the fine delay control circuitry 116, and the hyperfine delay control circuitry 118 may be configured to control the processing circuitry 103 to implement elevational beamforming. In particular, the coarse delay control circuitry 114, the fine delay control circuitry 116, and the hyperfine delay control circuitry 118 may be configured to introduce delays into ultrasound data received at different elevational channels, and the delays may be different for different elevational channels.

The coarse delay control circuitry 114 may be configured to introduce delays at a coarser resolution than the fine delay control circuitry 116 and hyperfine delay control circuitry 118. The coarse delay control circuitry 114 may control the memory 110 such that ultrasound data from different elevational channels may be summed with stored ultrasound data in the memory 110 that was collected at different times. For example, ultrasound data from one elevational channel that was collected at time $t_1$ may be summed with stored ultrasound data in the memory 110 that was collected at time $t_2$ while ultrasound data from another elevational channel that was collected at time $t_1$ may be summed with stored ultrasound data in the memory 110 that was collected at time $t_3$. Thus, the coarse delay control circuitry 114 may implement delays by changing the target address in the memory 110 for ultrasound data from each of the elevational channels (i.e., from each of the ADCs 102). Since each address in the memory 110 may correspond to a time based on the address counter, which runs at a rate of $f_{ADC}/D$, the minimum delay resolution provided by the coarse delay control circuitry 114 may be $D/f_{ADC}$.

For implementing a fixed delay that is determined at the beginning of ultrasound data acquisition and does not change throughout the acquisition, the fixed delay register storage circuitry 120 may store a register that includes a value for each of the elevational channels. For ultrasound data from each elevational channel, the coarse delay control circuitry 114 may retrieve the value corresponding to the elevational channel from the fixed delay register storage circuitry 120 and provide it at the ADDR terminal of the memory 110. As described above, the memory 110 may be configured to accumulate data in the memory 110 at an address that is the sum of the address counter and the data provided at the ADDR terminal. Since each address in the memory 110 may correspond to a time based on the address counter, accumulating data at an address in the memory 110 that is after the current address in the memory 110 may correspond to introducing a delay (which may be an advance or a retardation) into the data being accumulated in the memory 110. For implementing a dynamic delay that changes throughout the acquisition, in some embodiments the dynamic delay generation circuitry 122 may be configured to provide, to the coarse delay control circuitry 114, a dynamic value corresponding to the elevational channel, instead of the fixed delay register storage circuitry 120 providing a fixed value. In some embodiments, the dynamic delay generation circuitry 122 may be configured provide a dynamic value to the coarse delay control circuitry 114, which may be configured to add or subtract the dynamic value from the fixed delay provided by the fixed delay register storage circuitry 120 prior to providing the resulting sum to the ADDR terminal of the memory 110.

The fine delay control circuitry 116 may be configured to introduce delays at a coarser resolution than the hyperfine delay control circuitry 118 but at a finer resolution than the coarse delay control circuitry 114. The fine delay control circuitry 116 may control the CIC filter 108 such that ultrasound data from different elevational channels may be decimated with different phases. In other words, ultrasound data from one elevational channel may be decimated with one phase, and ultrasound data from another elevational channel may be decimated with another phase. The decimator 226 in the CIC filter 108 may have D choices (where D is the decimation rate of the decimator 226) for the output sample to feed to the comb stages 228 when decimating. Different choices for the output sample may effectively implement a delay. For example, if D=4, the decimator 226 may feed samples of ultrasound data from one elevational channel having indexes 0, 4, 8, etc., to the comb stages 228, while the decimator 226 may feed samples of ultrasound data from another elevational channel having indexes 1, 5, 9, etc., to the comb stages 228. In some embodiments that include sharing of a CIC filter 108, to make different choices for the output sample, the decimator 226 may include multiple counters, one for each shared elevational channel, and each of the counters may be initialized to a different value. When the decimator 226 is processing data from an elevational channel and that elevational channel's counter reaches a threshold value, the decimator 226 may output a sample. In some embodiments that include sharing of a CIC filter 108, to make different choices for the output sample, the decimator 226 may include a single counter and an adder configured to add the counter value to a value specific to the elevational channel being processed. When the sum from the adder reaches a threshold value, the decimator 226 may output a sample. Since the rate of the ultrasound data entering the CIC filter 108 is $f_{ADC}$, the minimum delay resolution provided by the fine delay control circuitry 116 may be $1/f_{ADC}$.

For implementing a fixed delay that is determined at the beginning of ultrasound data acquisition and does not change throughout the acquisition, the fixed delay register storage circuitry 120 may have a register that stores a value for each of the elevational channels. For ultrasound data from each elevational channel, the fine delay control circuitry 114 may retrieve the value corresponding to the elevational channel from the fixed delay register storage circuitry 120. In some embodiments, the fine delay control circuitry 114 may provide the value to a counter of the decimator 226 dedicated to that elevational channel. In some embodiments, the fine delay control circuitry 114 may provide the value to an adder configured to add the value to the value of a single counter of the decimator 226. For implementing a dynamic delay that changes throughout the acquisition, in some embodiments the dynamic delay generation circuitry 122 may be configured to provide, to the fine delay control circuitry 116, a dynamic value corresponding to the elevational channel, and the fine delay control circuitry 118 may be configured to add or subtract this dynamic value from the counter that corresponds to the elevational channel. This may cause the counter to output a sample earlier or later. Outputting a sample earlier may correspond to a reduced delay and outputting a sample later may correspond to an increased delay. If the fine delay control circuitry 116 were configured to simply increment or decrement a counter in between decimated output samples, this may cause a "glitch" due to the subtractors 236 in the comb stages 228 using an incorrect "past" value. To mitigate this, the fine delay control circuitry 116 may be configured to separate the values sent to the first delay stage 234 from the values sent to the first subtractor 236. In particular, the fine delay control circuitry 116 may be configured to ensure that that the value sent to the first subtractor 236 is in phase with respect to the sample coming out of the first delay register 234, and to ensure that the sample going into the first delay register 234 reflects the new phasing that is desired. In other words, the fine delay control circuitry 116 may be configured to control the decimator 226 to feed samples to the first subtractor 236 and the first delay register 234 at different clock cycles.

As an example, consider the decimation rate of the decimator 226 is D=3, the delay of the delay registers 234 is M=2, and a dynamic retardation delay of 1 sample is desired. Thus, the fine delay control circuitry 116 may be configured to subtract 1 from the decimation counter, causing the decimation counter to realign to a later phasing. Beforehand, the decimator 226 may have emitted every sample for which the sample index is i=0 mod 3, but after introducing the dynamic delay, the decimator 226 may emit samples for which the sample index is i=1 mod 3. However, the comb stages 228 may be filled with samples that are aligned with the original phase. Thus, for the next M=2 output samples, the fine delay control circuitry 116 may be configured to control the decimator 226 to output a sample aligned to the new phase into the first delay register 234, but to output a sample aligned with the previous phase into the first subtractor 236. For example, if the decimator 226 had fed samples with index 0 and 3 into the first delay register 234, after introduction of the dynamic delay of 1, the fine delay control circuitry 216 may control the decimator 226 to feed samples with index 6 and 9 into the subtractor 236 but to feed samples with index 7 and 10 into the delay register 236, after which the fine delay control circuitry 116 may control the decimator 226 to continue using the new phase. This example is illustrated in the table below:

TABLE 1

Example of sample indexes fed by the decimator to the subtractor and delay register for a dynamic fine delay

| ADC Sample Index | Fine Delay | Output Sample Index to the Subtractor | Output Sample Index to the Delay Register |
|---|---|---|---|
| 0 | 0 | 0 | 0 |
| 1 | 0 | 0 | 0 |
| 2 | 0 | 0 | 0 |
| 3 | 0 | 3 | 3 |
| 4 | 0 | 3 | 3 |
| 5 | 0 | 3 | 3 |
| 6 | 1 | 6 | 7 |
| 7 | 1 | 6 | 7 |
| 8 | 1 | 6 | 7 |
| 9 | 1 | 9 | 10 |
| 10 | 1 | 9 | 10 |
| 11 | 1 | 9 | 10 |
| 12 | 1 | 13 | 13 |
| 13 | 1 | 13 | 13 |
| 14 | 1 | 13 | 13 |

It should be appreciated that the delay value implemented here may only take effect after M output samples, since at the time of the introduction of the dynamic delay, there may already be M samples in the CIC filter 108 pipeline with the previous delay value. The coarse delay control circuitry 114, the fine delay control circuitry 116, and the hyperfine delay control circuitry 118 may coordinate introduction of dynamic delays such that the fine delay is introduced M samples early with respect to the coarse or hyperfine delays.

The hyperfine delay control circuitry 118 may be configured to introduce delays at a finer resolution than the coarse delay control circuitry 114 and the fine delay control circuitry 116. The hyperfine delay control circuitry 118 may be configured to control the DDS circuitry 104 to add a different phase offset to the complex signal generated by the DDS circuitry 104 for multiplying with ultrasound data from different elevational channels. In other words, one phase offset may be added to ultrasound data from one elevational channel, and another phase offset may be added to ultrasound data from another elevational channel. For narrow band signals or small delays $\tau$, $f(t-\tau) \approx e^{-i\omega\tau} f(t)$. In other words, a delay $\tau$ of a signal $f(t)$ may be implemented by multiplying $f(t)$ by $e^{-i\omega\tau}$. As described above, the DDS circuitry 104 and the multiplier 106 may be already configured to multiply the ultrasound data by $e^{i\omega_{DDS} t}$. The hyperfine delay control circuitry 118 may be configured to implement a delay by adding, for each elevational channel, a different offset to the waveform used for multiplication, so that the ultrasound data is instead multiplied by $e^{-i\omega_{DDS}(t-\tau)}$. For example, ultrasound data from one elevational channel may be multiplied by $e^{-i\omega_{DDS}(t-\tau 1)}$ while ultrasound data from another elevational channel may be multiplied by $e^{-i\omega_{DDS}(t-\tau 2)}$. As described above, for generating digital sinusoidal waveforms for forming complex signals, the DDS circuitry 104 may include a DDS phase counter, the value of which may be used in sine and/or cosine circuits. In some embodiments that include sharing of a multiplier 106, the DDS circuitry 104 may include multiple DDS phase counters, one for each shared elevational channel, and each of the DDS phase counters may be initialized to a different value that, upon being used by the DDS circuitry 104, provides the delay $\tau$. When the multiplier 106 is processing data from a specific elevational channel, the multiplier 106 may multiply the data by a complex signal formed based on waveforms from the DDS circuitry 104 when using that elevational channel's DDS phase counter. In some embodiments that include sharing of a multiplier 106, the DDS circuitry 104 may include a single DDS phase counter and an adder configured to add the DDS phase counter value to a value specific to the elevational channel being processed.

For implementing a fixed delay that is determined at the beginning of ultrasound data acquisition and does not change throughout the acquisition, the fixed delay register storage circuitry 120 may have a register that stores a value for each of the elevational channels. For ultrasound data from each elevational channel, the hyperfine delay control circuitry 118 may be configured to retrieve the value corresponding to the elevational channel from the fixed delay register storage circuitry 120. In some embodiments, the hyperfine delay control circuitry 116 may be configured to provide the value to a DDS phase counter of the DDS circuitry 104 dedicated to that elevational channel. In some embodiments, the hyperfine delay control circuitry 116 may be configured to provide the value to an adder configured to add the value to the value of a single DDS phase counter of the DDS circuitry 104. The minimum delay resolution provided by the hyperfine delay control circuitry 118 may be limited by the resolution of the DDS phase counter $B_{DDS}$ such that the minimum delay resolution is $1/(f_{DDS}B_{DDS})$.

For implementing a dynamic delay that changes throughout the acquisition, in some embodiments the dynamic delay generation circuitry 122 may be configured to provide, to the hyperfine delay control circuitry 118, a dynamic value corresponding to the elevational channel, and the hyperfine delay control circuitry 118 may be configured to add or subtract this dynamic value from the DDS phase counter that corresponds to the elevational channel.

In some embodiments, the registers in the fixed delay register storage circuitry 120 may store values for each elevational channel such that an arbitrary delay $\Delta T$ for an elevational channel may be broken up into $\Delta T_{coarse}$, $\Delta T_{fine}$, $\Delta T_{hyperfine}$, where $\Delta T = \Delta T_{coarse} + \Delta T_{fine} + \Delta T_{hyperfine}$. $\Delta T_{coarse}$ may be calculated by truncating $\Delta T$ to the nearest multiple of $D/f_{ADC}$ and selecting a value for the coarse delay register accordingly. A first remainder, equal to the difference between $\Delta T$ and the nearest multiple of $D/f_{ADC}$ may be calculated. $\Delta T_{fine}$ may be calculated by truncating the first remainder to the nearest multiple of $1/f_{ADC}$ and selecting a value for the fine delay register accordingly. A second remainder, equal to the difference between the first remainder and the nearest multiple of $1/f_{ADC}$, may be calculated. $\Delta T_{hyperfine}$ may be calculated by truncating the second remainder to the nearest DDS phase offset and selecting a value for the hyperfine delay register accordingly. In some embodiments, a subset of coarse, fine, and hyperfine delays may be used. For example, if only coarse and hyperfine delays are used, then $\Delta T_{coarse}$ may be calculated as above, and $\Delta T_{hyperfine}$ may be calculated by truncating the first remainder to the nearest DDS phase offset and selecting a value for the hyperfine delay register accordingly.

In some embodiments, a subset of the coarse delay control circuitry 114, the fine delay control circuitry 116, and the hyperfine delay control circuitry 118 may be preset in the datapath 100. For example, the datapath 100 may not include the coarse delay control circuitry 114, not include the fine delay control circuitry 116, not include the hyperfine delay control circuitry 118, not include the coarse delay control circuitry 116 or fine delay control circuitry 114, not include the coarse delay control circuitry 116 or hyperfine delay control circuitry 118, or not include the fine delay control circuitry 114 or hyperfine delay control circuitry 118.

In some embodiments, the dynamic time delay $\tau$ may be calculated according to the following "distance to source" equation:

$$\tau(t, y) = \frac{d(t)}{c} = \frac{\sqrt{y^2 + (ct)^2}}{c} = \sqrt{\left(\frac{y}{c}\right)^2 + t^2},$$

where y is fixed per elevational channel, c is the speed of sound, and t represents the time of the current sample and evolves dynamically.

In some embodiments, the dynamic delay parameters required for each sample may be stored (e.g., in dynamic delay register circuitry not shown in the figures). In some embodiments, the dynamic delay generation circuitry 122 may be configured to calculate the dynamic delay in real-time, which may involve some approximation. Once the dynamic delay generation circuitry 122 has calculated $\tau$, the dynamic delay generation circuitry 122 may be configured to split $\tau$ into coarse, fine, and/or hyperfine delays in the manner described above for $\Delta T_{coarse}$, $\Delta T_{fine}$, and $\Delta T_{hyperfine}$, and provide these dynamic delays to the coarse control circuitry 114, the fine control circuitry 116, and/or the hyperfine control circuitry 118.

In some embodiments, the dynamic delay generator circuitry 122 may be configured to use a CORDIC (Coordinate Rotation Digital Computer) algorithm to calculate τ in real-time. In such embodiments, the x component of the CORDIC rotation vector may be initialized to t from the above dynamic delay equation and the y may be initialized to y/c from the above dynamic delay equation. For each successive rotation of the vector, the x and y components of the vector may be computed according to the following equations:

$$x_{i+1} = x_i - y_i \cdot d_i \cdot 2^{-1}$$

$$y_{i+1} = y_i + x_i \cdot d_i \cdot 2^{-1}$$

$$d_i = -1 \text{ if } y_i \geq 0, 1 \text{ if } y_i < 0.$$

With successive rotations, y may approach 0 and x may approach $$A\sqrt{\left(\frac{y}{c}\right)^2 + t^2}.$$

Thus, the dynamic delay generation circuitry 122 may calculate $$\sqrt{\left(\frac{y}{c}\right)^2 + t^2}$$

by calculating x using the CORDIC algorithm. In some embodiments, the gain factor A may be fixed based on the number of iterations performed with the CORDIC algorithm. In some embodiments, circuitry include a multiplier or a fixed shift and add circuit may be configured to eliminate this gain factor A from the calculation. In some embodiments, software may be configured to eliminate this gain factor A from the calculation. In performing these calculations, the dynamic delay generation circuitry 120 may be programmed with the evolution rate t, or may derive it (e.g., using a multiplier and a programmable ADC clock rate, or using software and a register). The dynamic delay generation circuitry 120 may be programmed with values for y/c to allow for different sound speeds or to correct for lens effects.

In some embodiments, the dynamic delay generator circuitry 122 may be configured to use piecewise linear approximation to calculate T. In such embodiments, a lookup table may store values for key points along the delay curve expressed in the equation for τ above, and the dynamic delay generator circuitry 122 may calculate values at other points along the delay curve using linear interpolation. In particular, around a given time delay $t_0$, the equation for τ at a time t0+t can be approximated according to the following equation:

$$\tau(t_0 + t, y) \approx \tau(t_0, y) + \frac{2t}{\left(\frac{y}{c}\right)^2 + t_0^2} = \tau(t_0, y) + \gamma(t_0, y)t,$$

$$\text{where } \gamma(t_0, y) = \frac{2}{\left(\frac{y}{c}\right)^2 + t_0^2}.$$

The lookup table (which may be stored, for example, in dynamic delay register circuitry not shown in the figures) may store $\tau(t_0, y)$ and $\gamma(t_0, y)$ for several points to along the delay curve expressed in the equation for τ above. In some embodiments, the dynamic delay generator circuitry 122 may calculate $\gamma(t_0, y)t$ using a variable rate accumulator. This accumulator may be variable rate in that it may be a counter that can implement different slopes. In some embodiments, higher order polynomial approximations may be used. In such embodiments, multiple counters may be used based, where the number of counters depends on the order, and the increment value of one counter (namely, the amount by which the counter increments on a clock cycle) may come from the output of another counter.

In some embodiments, more complex equations for delay, such as equations that account for lens curvature or use approximations that increase the size of the focal region, may be used. In some embodiments, a memory giving arbitrary delays at arbitrary times may be used.

Figure 3:
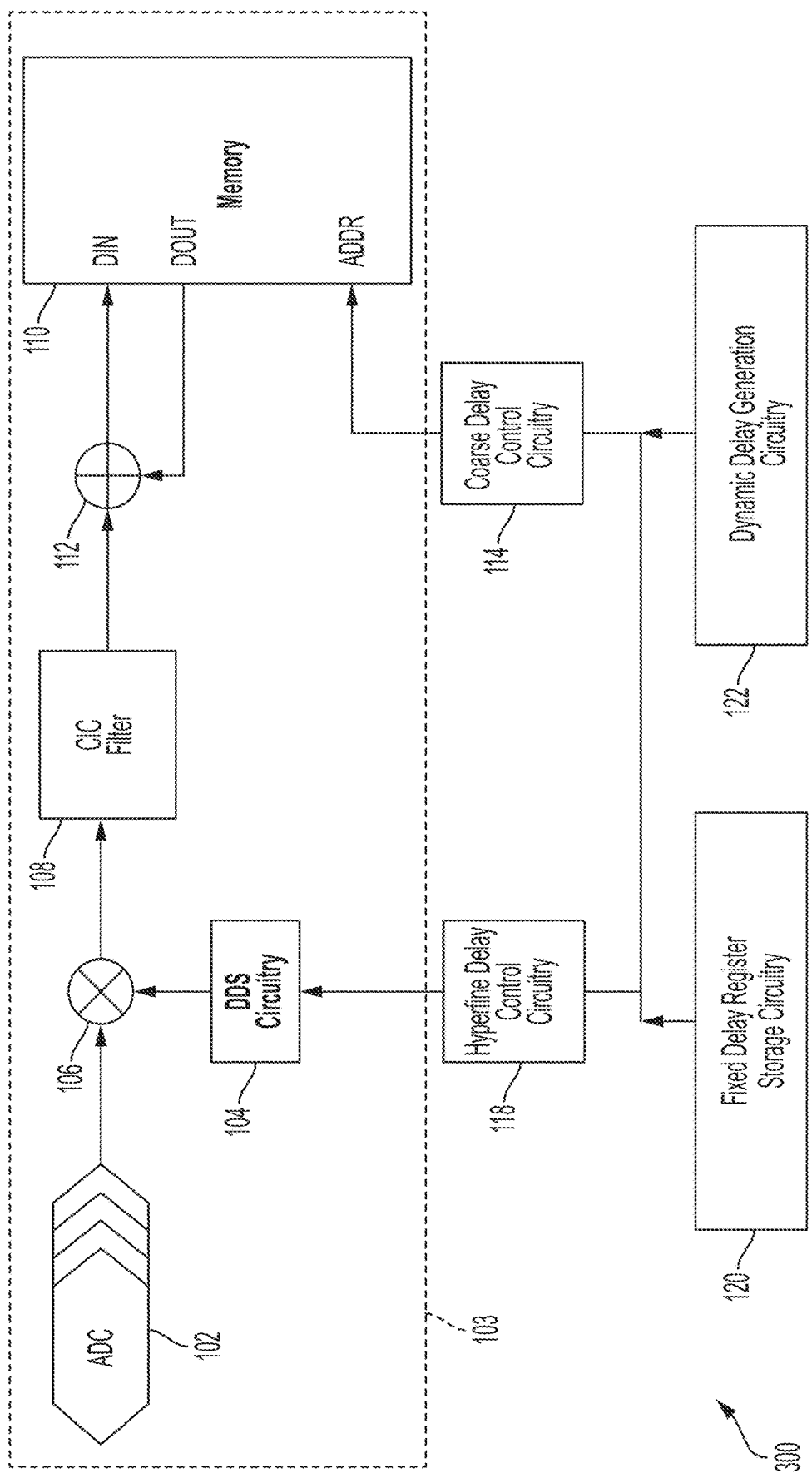
FIG. 3 illustrates another example datapath for ultrasound data received by an ultrasound device, in accordance with certain embodiments described herein.

FIG. 3 illustrates another example datapath 300 for ultrasound data received by an ultrasound device, in accordance with certain embodiments described herein. The datapath 300 is the same as the datapath 100, except that the datapath 300 lacks the fine delay control circuitry 116. Thus, the coarse delay control circuitry 114 and the hyperfine delay control circuitry 118 may be configured to control the processing circuitry 103 to implement elevational beamforming. In some embodiments, the registers in the fixed delay register storage circuitry 120 may store values for each elevational channel such that an arbitrary delay $\Delta T$ for an elevational channel may be broken up into $\Delta T_{coarse}$ and $\Delta T_{hyperfine}$, where $\Delta T = \Delta T_{coarse} + \Delta T_{hyperfine}$. $\Delta T_{coarse}$ may be calculated by truncating $\Delta T$ to the nearest multiple of $D/f_{ADC}$ and selecting a value for the coarse delay register accordingly. A first remainder, equal to the difference between $\Delta T$ and the nearest multiple of $D/f_{ADC}$ may be calculated. $\Delta T_{hyperfine}$ may be calculated by truncating the first remainder to the nearest DDS phase offset and selecting a value for the hyperfine delay register accordingly.

Figure 4:
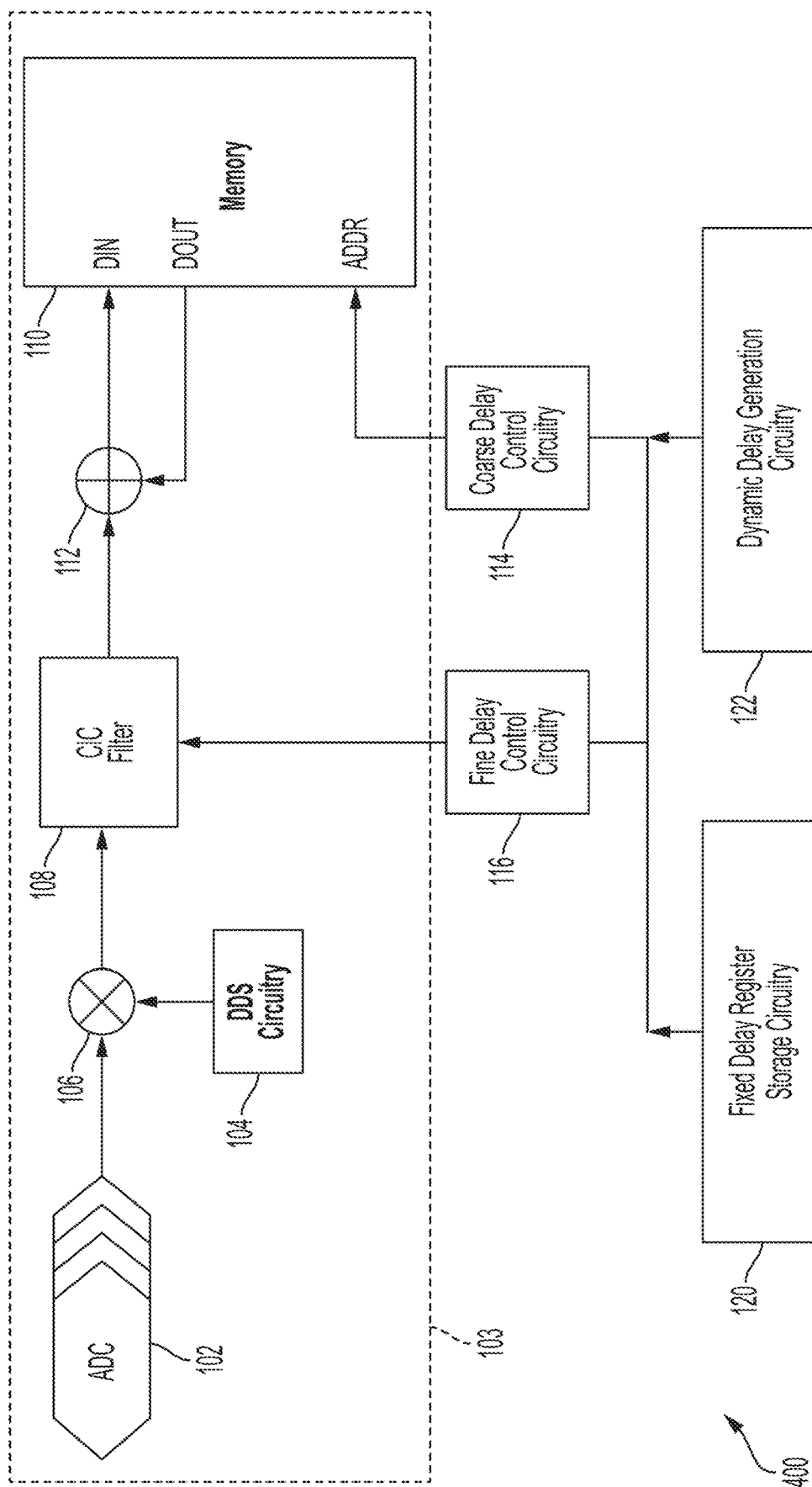
FIG. 4 illustrates another example datapath for ultrasound data received by an ultrasound device, in accordance with certain embodiments described herein.

FIG. 4 illustrates another example datapath 400 for ultrasound data received by an ultrasound device, in accordance with certain embodiments described herein. The datapath 300 is the same as the datapath 100, except that the datapath 400 lacks the hyperfine delay control circuitry 118. Thus, the coarse delay control circuitry 114 and the fine delay control circuitry 116 may be configured to control the processing circuitry 103 to implement elevational beamforming. In some embodiments, the registers in the fixed delay register storage circuitry 120 may store values for each elevational channel such that an arbitrary delay $\Delta T$ for an elevational channel may be broken up into $\Delta T_{coarse}$ and $\Delta T_{fine}$, where $\Delta T = \Delta T_{coarse} + \Delta T_{fine}$. $\Delta T_{coarse}$ may be calculated by truncating $\Delta T$ to the nearest multiple of $D/f_{ADC}$ and selecting a value for the coarse delay register accordingly. A first remainder, equal to the difference between $\Delta T$ and the nearest multiple of $D/f_{ADC}$ may be calculated. $\Delta T_{fine}$ may be calculated by truncating the first remainder to the nearest multiple of $1/f_{ADC}$ and selecting a value for the fine delay register accordingly.

Figure 5:
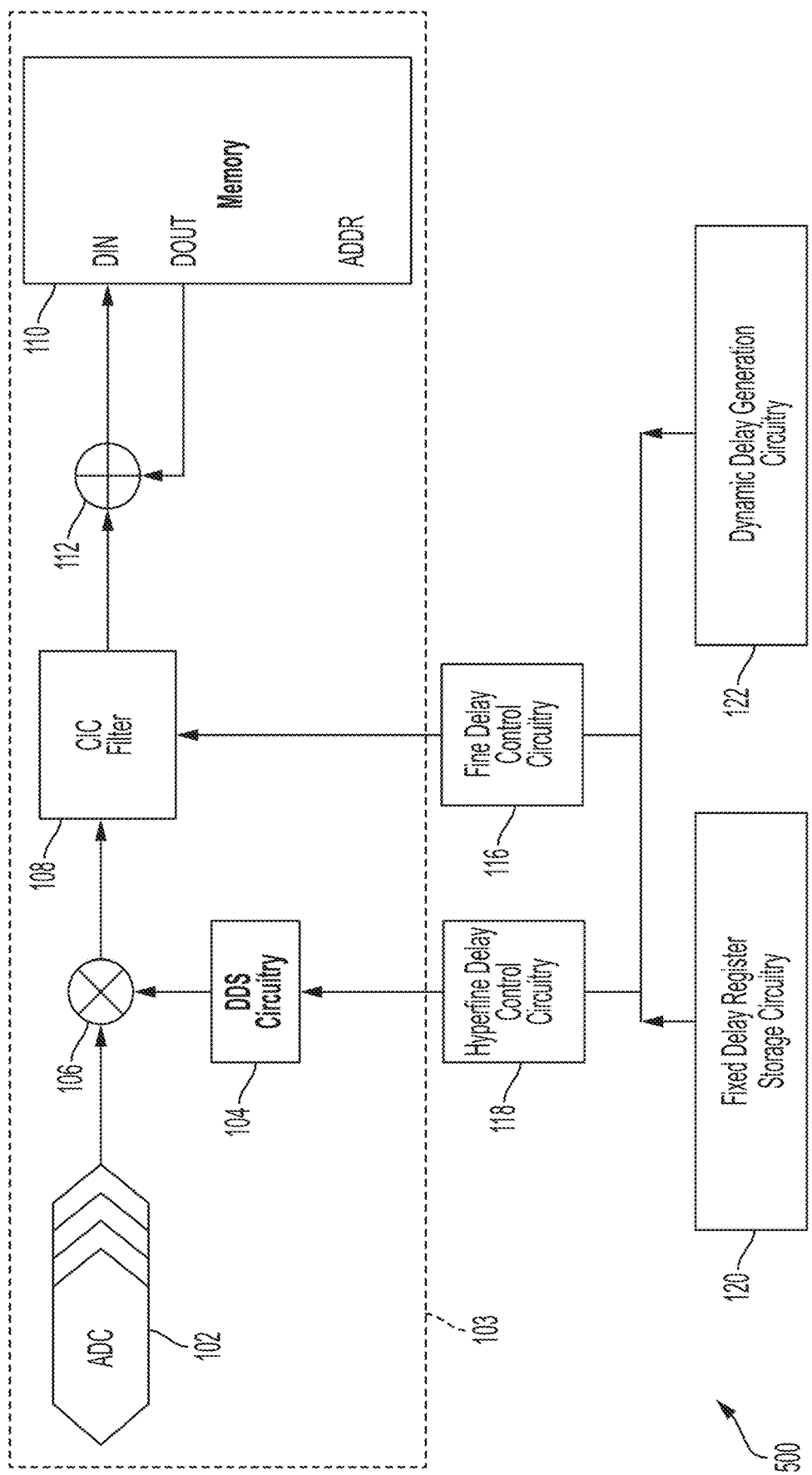
FIG. 5 illustrates another example datapath for ultrasound data received by an ultrasound device, in accordance with certain embodiments described herein.

FIG. 5 illustrates another example datapath 500 for ultrasound data received by an ultrasound device, in accordance with certain embodiments described herein. The datapath 500 is the same as the datapath 100, except that the datapath 500 lacks the coarse delay control circuitry 116. Thus, the fine delay control circuitry 116 and the hyperfine delay control circuitry 118 may be configured to control the processing circuitry 103 to implement elevational beamforming. In some embodiments, the registers in the fixed delay register storage circuitry 120 may store values for each elevational channel such that an arbitrary delay $\Delta T$ for an elevational channel may be broken up into $\Delta T_{fine}$ and $\Delta T_{hyperfine}$, where $\Delta T = \Delta T_{fine} + \Delta T_{hyperfine}$. $\Delta T_{fine}$ may be calculated by truncating the $\Delta T$ to the nearest multiple of $1/f_{ADC}$ and selecting a value for the fine delay register accordingly. A first remainder, equal to the difference between the first remainder and the nearest multiple of $1/f_{ADC}$, may be calculated. $\Delta T_{hyperfine}$ may be calculated by truncating the first remainder to the nearest DDS phase offset and selecting a value for the hyperfine delay register accordingly.

Figure 6:
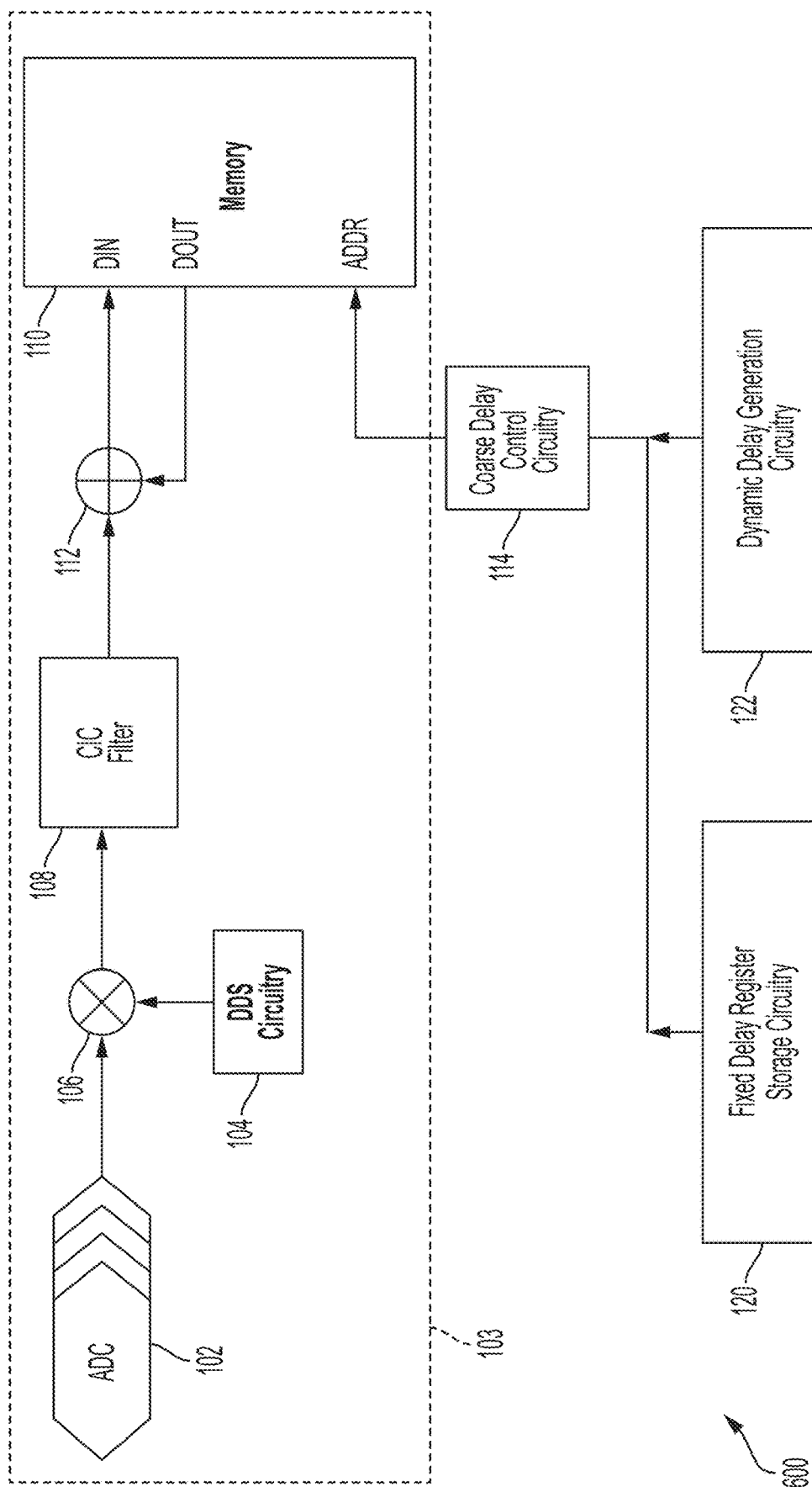
FIG. 6 illustrates another example datapath for ultrasound data received by an ultrasound device, in accordance with certain embodiments described herein.

FIG. 6 illustrates another example datapath 600 for ultrasound data received by an ultrasound device, in accordance with certain embodiments described herein. The datapath 600 is the same as the datapath 100, except that the datapath 600 lacks the fine delay control circuitry 116 and the hyperfine delay control circuitry 118. Thus, the coarse delay control circuitry 114 may be configured to control the processing circuitry 103 to implement elevational beamforming. A value for the coarse delay register in the fixed delay register storage circuitry 120 may be selected based on the desired delay $\Delta T$.

Figure 7:
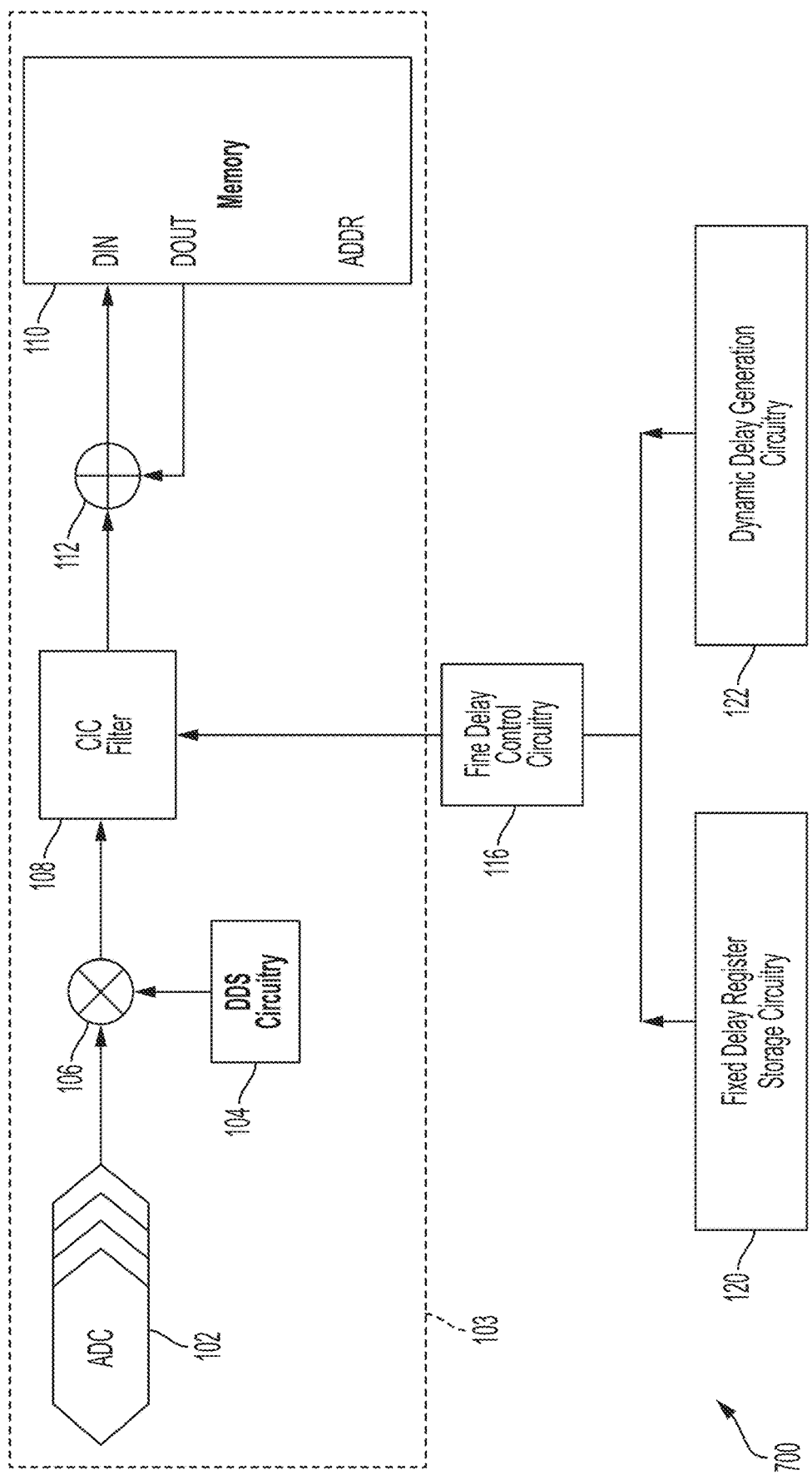
FIG. 7 illustrates another example datapath or ultrasound data received by an ultrasound device, in accordance with certain embodiments described herein.

FIG. 7 illustrates another example datapath 700 for ultrasound data received by an ultrasound device, in accordance with certain embodiments described herein. The datapath 700 is the same as the datapath 100, except that the datapath 700 lacks the coarse delay control circuitry 114 and the hyperfine delay control circuitry 118. Thus, the fine delay control circuitry 116 may be configured to control the processing circuitry 103 to implement elevational beamforming. A value for the fine delay register in the fixed delay register storage circuitry 120 may be selected based on the desired delay $\Delta T$.

Figure 8:
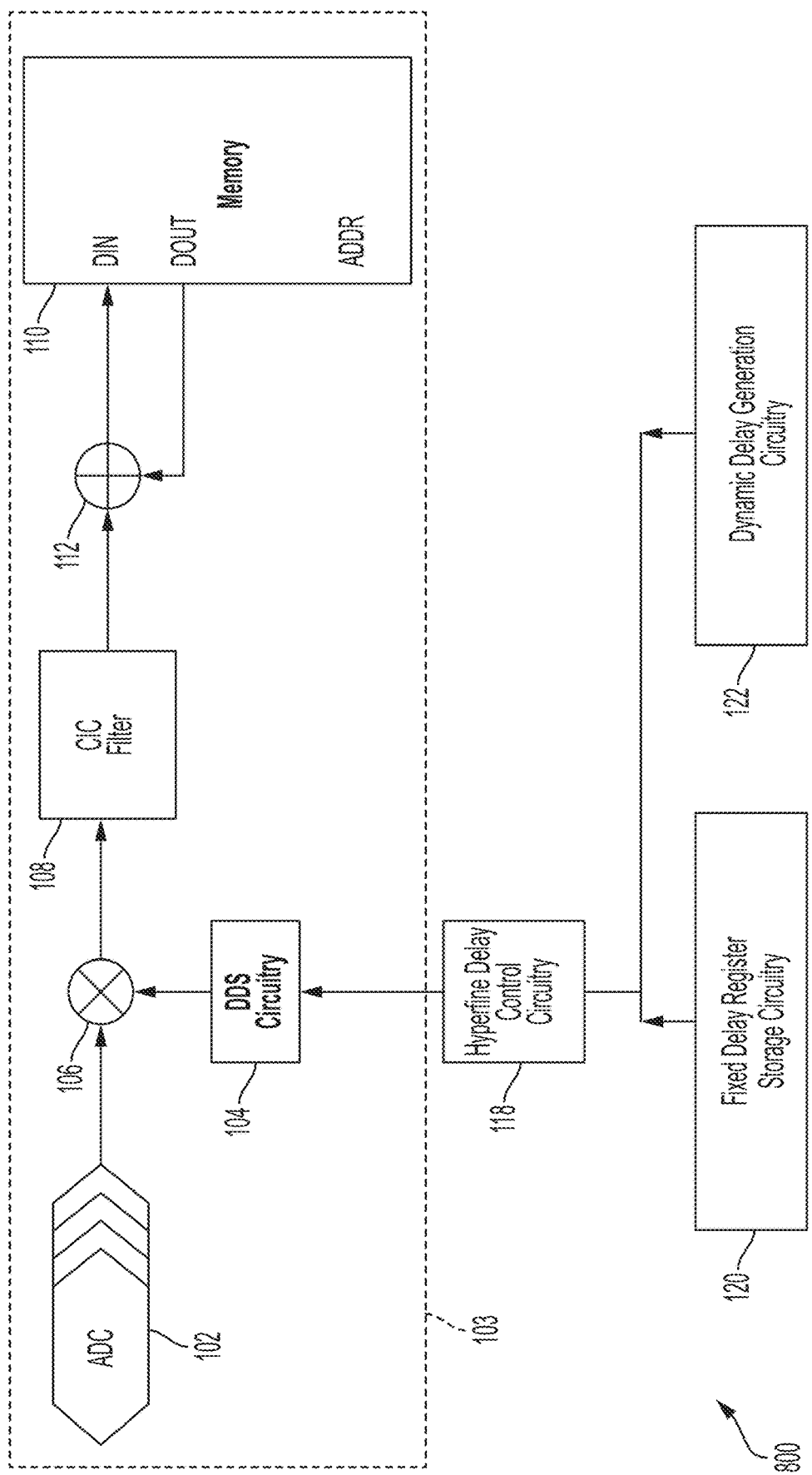
FIG. 8 illustrates another example datapath for ultrasound data received by an ultrasound device, in accordance with certain embodiments described herein.

FIG. 8 illustrates another example datapath 800 for ultrasound data received by an ultrasound device, in accordance with certain embodiments described herein. The datapath 800 is the same as the datapath 100, except that the datapath 800 lacks the coarse delay control circuitry. Thus, the hyperfine delay control circuitry 118 may be configured to control the processing circuitry 103 to implement elevational beamforming. A value for the hyperfine delay register in the fixed delay register storage circuitry 120 may be selected based on the desired delay $\Delta T$.

Figure 9:
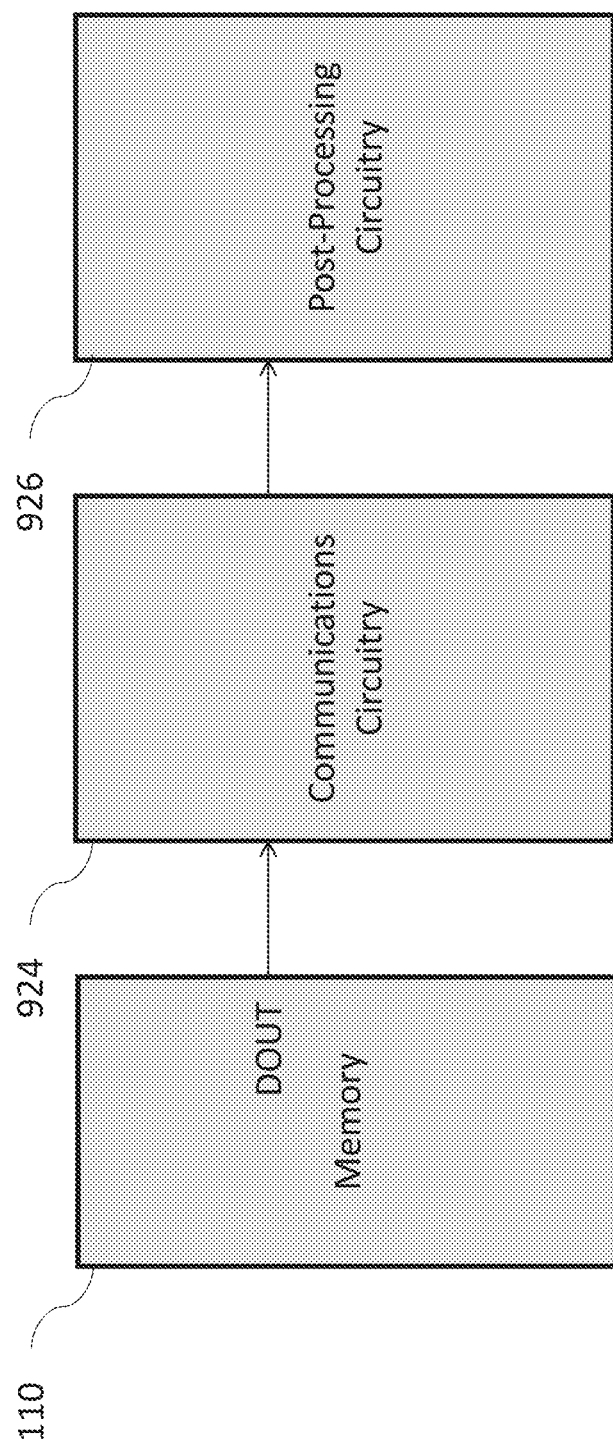
FIG. 9 illustrates an example of a downstream portion of any of the datapaths described herein, in accordance with certain embodiments described herein.

FIG. 9 illustrates an example of a downstream portion of any of the datapaths described herein, in accordance with certain embodiments described herein. The DOUT terminal of the memory 110 is coupled to the input terminal of communications circuitry 924. The output terminal of the communications circuitry 924 is coupled to the input terminal of post-processing circuitry 926. The communications circuitry 924 may be configured to transmit data from the memory 110 to the post-processing circuitry 926 and may include, for example, circuitry capable of transmitting data over a communications link such as a Universal Serial Bus (USB) communications link, a serial-deserializer (SerDes) link, or a wireless link (e.g., a link employing the IEEE 802.11 standard). Thus, the communications circuitry 926 may be coupled to the post-processing circuitry 926 through a USB communications link (e.g., a cable) or through a SerDes communications link. The post-processing circuitry 926 may be configured to post-process ultrasound data after it has been stored in the memory 110, and may include, for example, circuitry for summing, requantization, noise shaping, waveform removal, image formation, and backend processing. In some embodiments, the memory 110 and the communications circuitry 924 may be located on an ultrasound-on-a-chip while the post-processing circuitry 926 may be located on a separate electronic device (e.g., a field-programmable gate array (FPGA) device) to which the ultrasound-on-a chip is coupled. In some embodiments, the memory 110 and the communications circuitry 924 may be located on an ultrasound probe while the post-processing circuitry 926 may be located on a host device to which the ultrasound probe is coupled.

Figure 10:
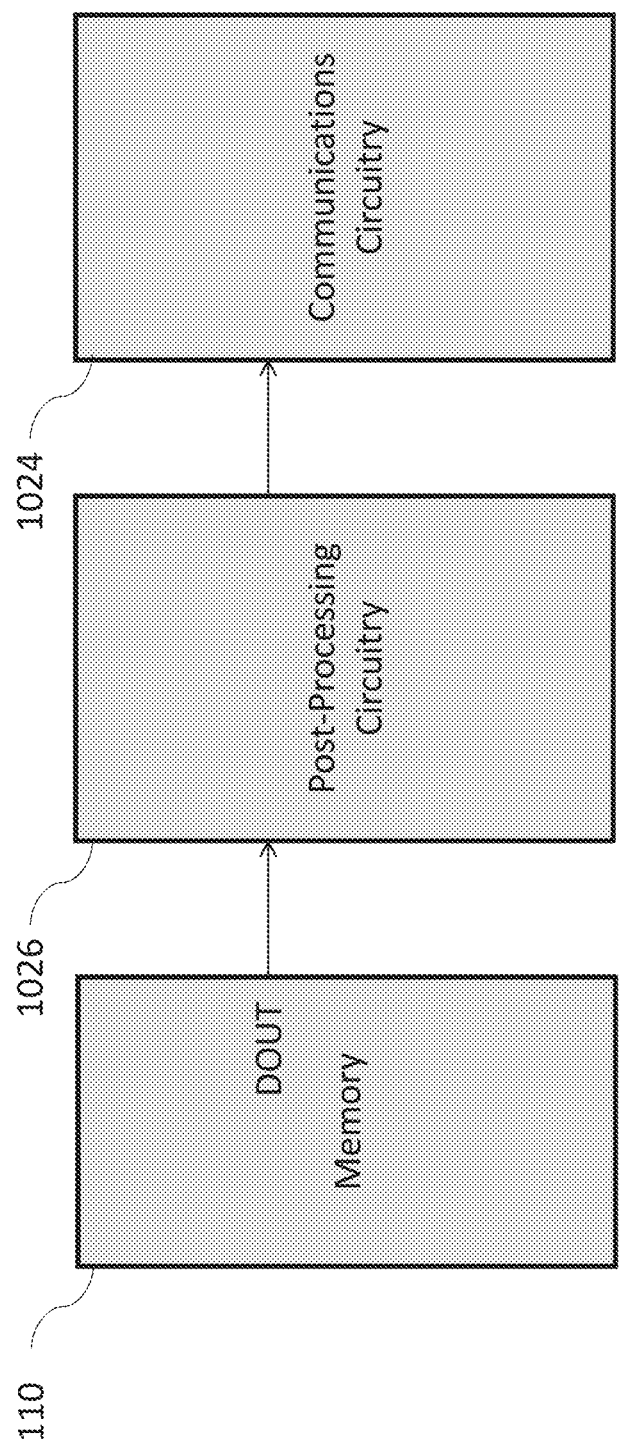
FIG. 10 illustrates an example of a downstream portion of any of the datapaths described herein, in accordance with certain embodiments described herein.

FIG. 10 illustrates another example of a downstream portion of any of the datapaths described herein, in accordance with certain embodiments described herein. The DOUT terminal of the memory 110 is coupled to the input terminal of post-processing circuitry 1026. The output terminal of the post-processing circuitry 1026 is coupled to the input terminal of the communications circuitry 1024. The communications circuitry 1024 may be configured to transmit data from the post-processing circuitry 1026 to another electronic device, such as a host device or an FPGA, and may include, for example, circuitry capable of transmitting data over a communications link such as a Universal Serial Bus (USB) communications link, a serial-deserializer (SerDes) link, or a wireless link (e.g., a link employing the IEEE 802.11 standard). The post-processing circuitry 1026 may be configured to post-process ultrasound data after it has been stored in the memory 110, and may include, for example, circuitry for summing, requantization, noise shaping, waveform removal, image formation, and backend processing. In some embodiments, the memory 110, the post-processing circuitry 1026, and the communications circuitry 1024 may be located on an ultrasound-on-a-chip. In some embodiments, the memory 110, the post-processing circuitry 1026, and the communications circuitry 1024 may be located on an ultrasound probe.

Figure 11:
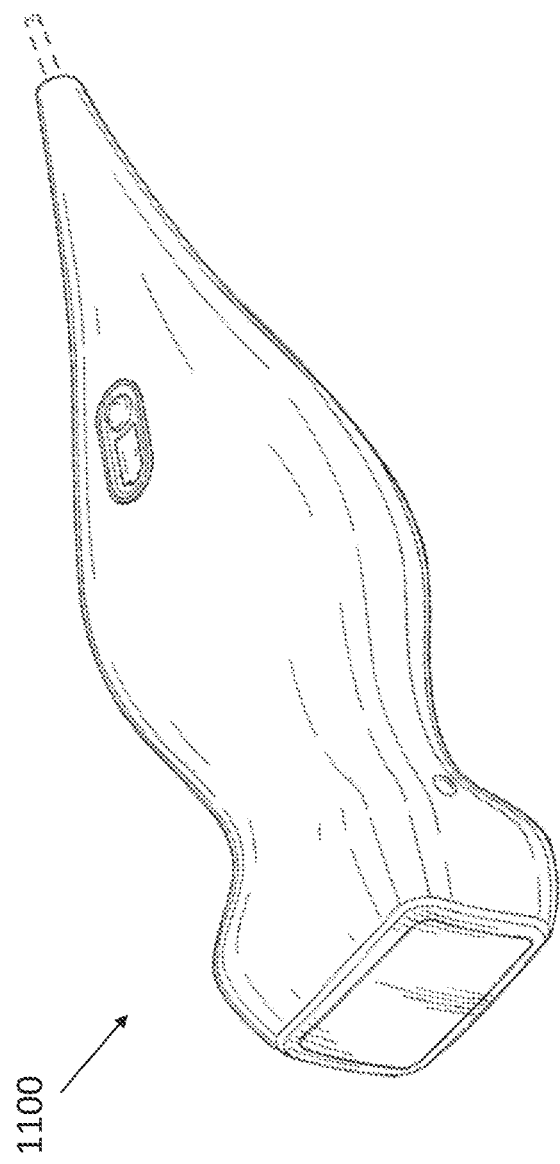
FIG. 11 illustrates an example handheld ultrasound probe in which an ultrasound-on-a-chip may be disposed, in accordance with certain embodiments described herein.

FIG. 11 illustrates an example handheld ultrasound probe 1100 in which an ultrasound-on-a-chip may be disposed, in accordance with certain embodiments described herein. The ultrasound-on-a-chip in the handheld ultrasound probe 1100 may include all the circuitry of any datapath described herein.

Figure 12:
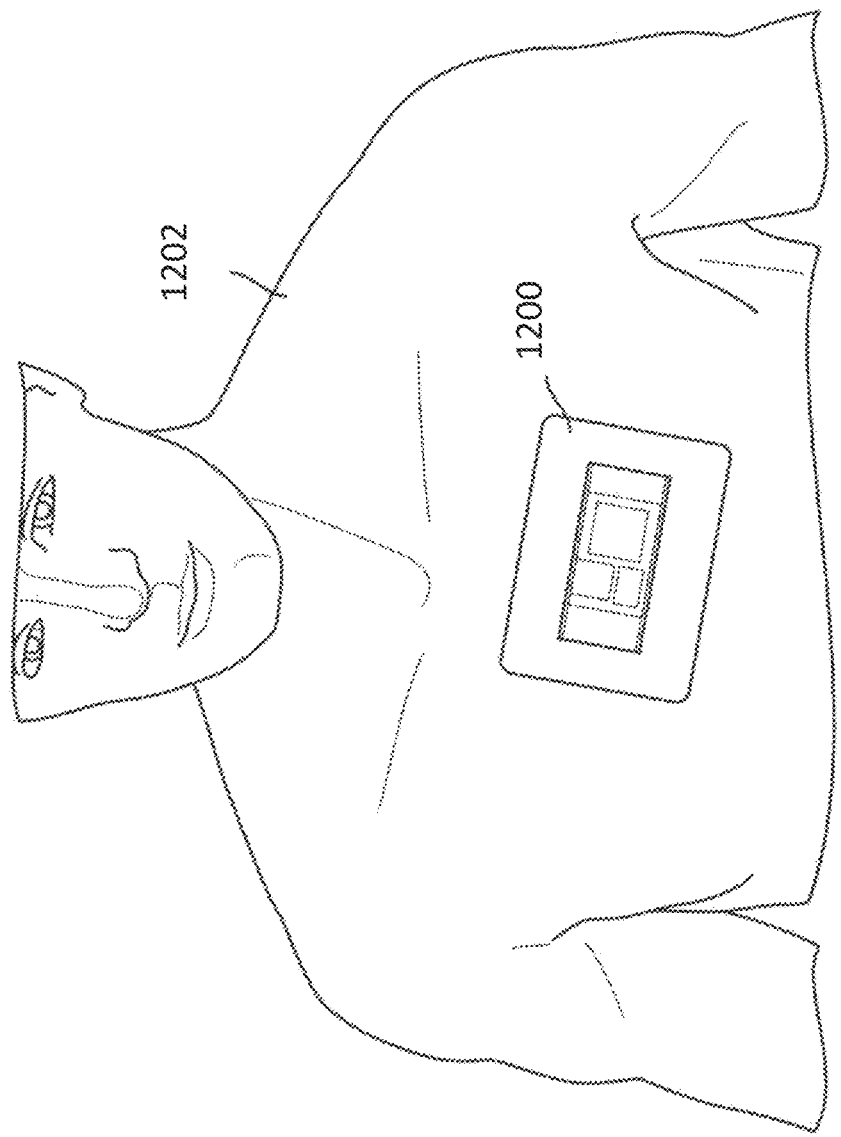
FIG. 12 illustrates an example ultrasound patch in which an ultrasound-on-a-chip may be disposed, in accordance with certain embodiments described herein.

FIG. 12 illustrates an example ultrasound patch 1200 in which an ultrasound-on-a-chip may be disposed, in accordance with certain embodiments described herein. The ultrasound patch 1200 is coupled to a subject 1202. The ultrasound-on-a-chip in the ultrasound patch 1200 may include all the circuitry of any datapath described herein.

Figure 13:
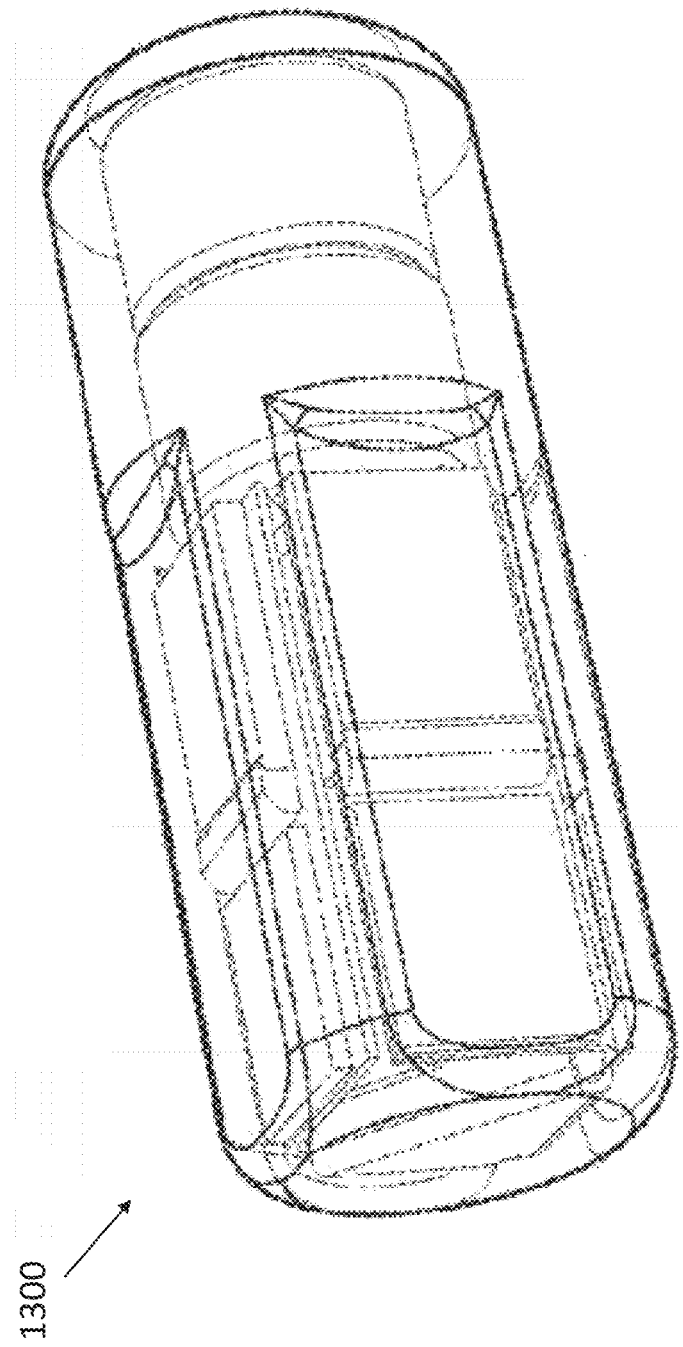
FIG. 13 illustrates an example ultrasound pill in which an ultrasound-on-a-chip may be disposed, in accordance with certain embodiments described herein.

FIG. 13 illustrates an example ultrasound pill 1300 in which an ultrasound-on-a-chip may be disposed, in accordance with certain embodiments described herein. The ultrasound-on-a-chip in the ultrasound patch 1300 may include all the circuitry of any datapath described herein.

Further description of the handheld ultrasound probe 1100, the ultrasound patch 1200, and the ultrasound pill 1300 may be found in U.S. patent application Ser. No. 15/626,711 titled "UNIVERSAL ULTRASOUND IMAGING DEVICE AND RELATED APPARATUS AND METHODS," filed on Jun. 19, 2017 and published as U.S. Pat. App. Publication No. 2017-0360399 A1 (and assigned to the assignee of the instant application).

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps.

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An ultrasound device, comprising:
processing circuitry; and
control circuitry configured to control the processing circuitry to perform elevational beamforming, wherein:
the control circuitry and the processing circuitry are disposed on an ultrasound-on-a-chip in the ultrasound device;
the processing circuitry comprises a decimator; and
the control circuitry is configured to control the decimator to decimate first ultrasound data from a first elevational channel to impart the first ultrasound data with a first phase and to decimate second ultrasound data from a second elevational channel to impart the second ultrasound data with a second phase,
wherein the control circuitry is configured to control the decimator to implement a portion of a delay of ultrasound data from at least one of the first and second elevational channels.

2. The ultrasound device of claim 1, wherein the ultrasound-on-a-chip is disposed within a patch.

3. The ultrasound device of claim 1, wherein:
the control circuitry is configured to control the processing circuitry to perform elevational beamforming on ultrasound data, wherein the processing circuitry is in a portion of a datapath that is subsequent to conversion of the ultrasound data from analog to digital and prior to or concurrent with saving of the ultrasound data to memory.

4. The ultrasound device of claim 1, wherein the ultrasound device comprises a handheld ultrasound probe.

5. The ultrasound device of claim 1, wherein:
the processing circuitry comprises a memory; and
the control circuitry is configured to control the memory such that first ultrasound data from a first elevational channel that was collected at a first time is summed with stored ultrasound data in the memory that was collected at a second time, and second ultrasound data from a second elevational channel that was collected at the first time is summed with stored ultrasound data in the memory that was collected at a third time.

6. The ultrasound device of claim 5, wherein the control circuitry is configured to control an address for reading the stored ultrasound data in the memory that was collected at a second time from the memory and for writing to the memory the summed ultrasound data formed by summing the first ultrasound data from a first elevational channel that was collected at a first time with the stored ultrasound data in the memory that was collected at a second time.

7. The ultrasound device of claim 6, wherein:
the memory further comprises an address counter;
the control circuitry is configured to provide a value to the memory; and
the address for reading the stored ultrasound data in the memory that was collected at a second time from the memory and for writing to the memory the summed ultrasound data formed by summing the first ultrasound data from a first elevational channel that was collected at a first time with the stored ultrasound data in the memory that was collected at a second time is a sum of a current value of the address counter and the value provided by the control circuitry.

8. The ultrasound device of claim 7, wherein:
the ultrasound device further comprises a register storing a plurality of values each corresponding to one of the first and second elevational channels; and
the control circuitry is configured to retrieve the value provided by the control circuitry from amongst the plurality of values.

9. The ultrasound device of claim 1, wherein:
the decimator includes a counter for determining when the decimator outputs samples; and
the control circuitry is configured to provide a value to the counter.

10. The ultrasound device of claim 9, wherein the decimator includes one counter per elevational channel.

11. The ultrasound device of claim 9, wherein:
the ultrasound device further comprises a register storing a plurality of values each corresponding to one of the first and second elevational channels; and
the control circuitry is configured to retrieve the value provided by the control circuitry to the counter from amongst the plurality of values.

12. The ultrasound device of claim 1, further comprising a cascaded integrator-comb (CIC) filter that includes the decimator.

13. The ultrasound device of claim 12, wherein the CIC filter includes a subtractor and a delay stage in a feedforward configuration following the decimator.

14. The ultrasound device of claim 13, wherein the control circuitry is further configured to control the decimator to clock samples into the subtractor and the delay stage at different clock cycles.

15. An ultrasound device, comprising:
processing circuitry comprising:
  a memory;
  a decimator;
  direct digital synthesis (DDS) circuitry; and
control circuitry comprising:
  first control circuitry configured to control the memory such that first ultrasound data from a first elevational channel that was collected at a first time is summed with stored ultrasound data in the memory that was collected at a second time, and second ultrasound data from a second elevational channel that was collected at the first time is summed with stored ultrasound data in the memory that was collected at a third time;
  second control circuitry configured to control the decimator to decimate the first ultrasound data from the first elevational channel to impart the first ultrasound data with a first phase and to decimate the second ultrasound data from the second elevational channel to impart the second ultrasound data with a second phase; and
  third control circuitry configured to control the DDS circuitry to add a first phase offset to a complex signal generated by the DDS circuitry for multiplying with first ultrasound data from the first elevational channel and to add a second phase offset to the complex signal generated by the DDS circuitry for multiplying with second ultrasound data from the second elevational channel; and
  wherein at least two of the first control circuitry, the second control circuitry, and the third control circuitry are each configured to control the processing circuitry to implement a portion of a delay of ultrasound data from one of the first and second elevational channels.

16. The ultrasound device of claim 15, wherein:
the control circuitry is further configured to control the processing circuitry to perform elevational beamforming; and
the control circuitry and the processing circuitry are disposed on an ultrasound-on-a-chip in the ultrasound device.

17. The ultrasound device of claim 16, wherein:
the DDS circuitry includes a DDS phase counter; and
the control circuitry is configured to provide a value to the DDS phase counter.

18. The ultrasound device of claim 17, wherein the DDS circuitry includes one DDS phase counter per elevational channel.

19. The ultrasound device of claim 17, wherein:
the ultrasound device further comprises a register storing a plurality of values each corresponding to one of the first and second elevational channels; and
the control circuitry is configured to retrieve the value it provides to the DDS phase counter from amongst the plurality of values.

* * * * *